(12) United States Patent
Fraatz et al.

(10) Patent No.: US 10,767,198 B2
(45) Date of Patent: Sep. 8, 2020

(54) METHOD FOR PRODUCING BRANCHED ALDEHYDES

(71) Applicant: SYMRISE AG, Holzminden (DE)

(72) Inventors: Marco A. Fraatz, Gießen (DE); Holger Zorn, Wettenberg (DE); Johanna Rost, Heidesheim (DE); Michael Goldmann, Schackau (DE); Egon Gross, Holzminden (DE); Jakob Ley, Holzminden (DE); Katrin Geissler, Einbeck (DE); Torsten Geissler, Einbeck (DE); Michael Backes, Holzminden (DE); Fabia Hentschel, Holzminden (DE); Jens-Michael Hilmer, Holzminden (DE)

(73) Assignee: SYMRISE AG, Holzminden (DE)

( * ) Notice: Subject to any disclaimer, the term of this patent is extended or adjusted under 35 U.S.C. 154(b) by 55 days.

(21) Appl. No.: 15/779,214

(22) PCT Filed: Nov. 28, 2015

(86) PCT No.: PCT/EP2015/077992
§ 371 (c)(1),
(2) Date: Sep. 6, 2018

(87) PCT Pub. No.: WO2017/088937
PCT Pub. Date: Jun. 1, 2017

(65) Prior Publication Data
US 2019/0367954 A1 Dec. 5, 2019

(51) Int. Cl.
*C12P 7/24* (2006.01)
*C07C 45/27* (2006.01)
*C12N 9/02* (2006.01)

(52) U.S. Cl.
CPC .......... *C12P 7/24* (2013.01); *C07C 45/27* (2013.01); *C12N 9/0083* (2013.01)

(58) Field of Classification Search
CPC .................................................. C12N 9/0083
See application file for complete search history.

(56) References Cited

U.S. PATENT DOCUMENTS

| | | |
|---|---|---|
| 7,491,854 B2 | 2/2009 | Binder |
| 2013/0149756 A1* | 6/2013 | Sporleder ............ C12N 9/0069 435/147 |

FOREIGN PATENT DOCUMENTS

| | | |
|---|---|---|
| JP | H-02-086788 A | 3/1990 |
| JP | 2014-525741 A | 10/2014 |
| WO | 2012025629 A1 | 3/2012 |

OTHER PUBLICATIONS

International Search Report and Written Opinion dated Jul. 25, 2016 in corresponding PCT Application No. PCT/EP2015/077992.
Japanese Office Action dated May 11, 2020 for corresponding JP Application No. 2018- 527761.
Yuasa, Y. et al., "Convenient syntheses of iso-methyl-branched long-chain aliphatic aldehydes, known to contribute significantly to meat flavor," Flavour and Fragrance Journal, vol. 19, 2004, pp. 199-204.
D3—The Chemical Society, 1977.

* cited by examiner

Primary Examiner — Bin Shen
(74) Attorney, Agent, or Firm — Polsinelli PC

(57) ABSTRACT

A method for producing branched aldehydes is proposed, the method comprising the following steps:
(a) providing a culture of one or more fungi of the genus Conidiobolus and producing biomass containing branched carboxylic acids in free and/or bound form;
(b) extracting the biomass from step (a) to produce a first intermediate containing free and/or bound carboxylic acids;
(c) optionally chemically, enzymatically or microbially hydrolyzing the bound carboxylic acids from the first intermediate;
(d) treating the first intermediate with a reducing agent of a chemical nature to convert the free and/or bound carboxylic acids into the corresponding alcohols and optionally separating one or more alcohols from interfering by-products and producing the chemically produced second intermediate containing these alcohols as a mixture or in enriched form;
(e) treating the first intermediate with a reducing agent of a biological nature to convert the free and/or bound carboxylic acids into the corresponding aldehydes having the same number of carbon atoms compared to the free and/or bound carboxylic acids or into the corresponding aldehydes having a reduced number of carbon atoms by one compared to the free and/or bound carboxylic acids and producing the biologically produced second intermediate containing these aldehydes;
(f) treating the chemically produced second intermediate with an oxidizing agent of a chemical nature to convert the free and/or bound alcohols into the corresponding aldehydes; and optionally
(g) removing interfering by-components from the fractions obtainable after step(s) (d) and/or (e) and/or (f).

18 Claims, 11 Drawing Sheets

METHOD FOR PRODUCING BRANCHED ALDEHYDES

CROSS-REFERENCE TO RELATED APPLICATIONS

This application is a national stage application (under 35 U.S.C. § 371) of PCT/EP2015/077992, filed Nov. 28, 2015, which is incorporated herein by reference in its entirety.

FIELD OF INVENTION

The invention is in the field of flavoring substances and relates to a new method for the production of branched aldehydes, in particular 12-methyltridecanal.

STATE OF THE ART

Branched aldehydes are interesting odorous and flavoring substances that are prevalent in nature. 12-methyltridecanal in particular is an important building block for authentically tasting bovine flavors and can currently only be commercially produced by chemical synthesis (cf. Kerscher, et. al., *J. Agric. Food Chem.* 48(6), p. 2387-2390, 2000).

Based on the manufacturing process, it can therefore not be declared natural in the sense of European flavor legislation. On the other hand, there is a special interest on the market in flavors that can be declared not only as nature-identical, but explicitly as natural; this declaration option also represents an important purchase and price argument.

The objective of the present invention was therefore to provide a method for the production of branched aldehydes in general and 12-methyltridecanal in particular by biotechnological and therefore natural means.

DESCRIPTION OF THE INVENTION

Figure 1:
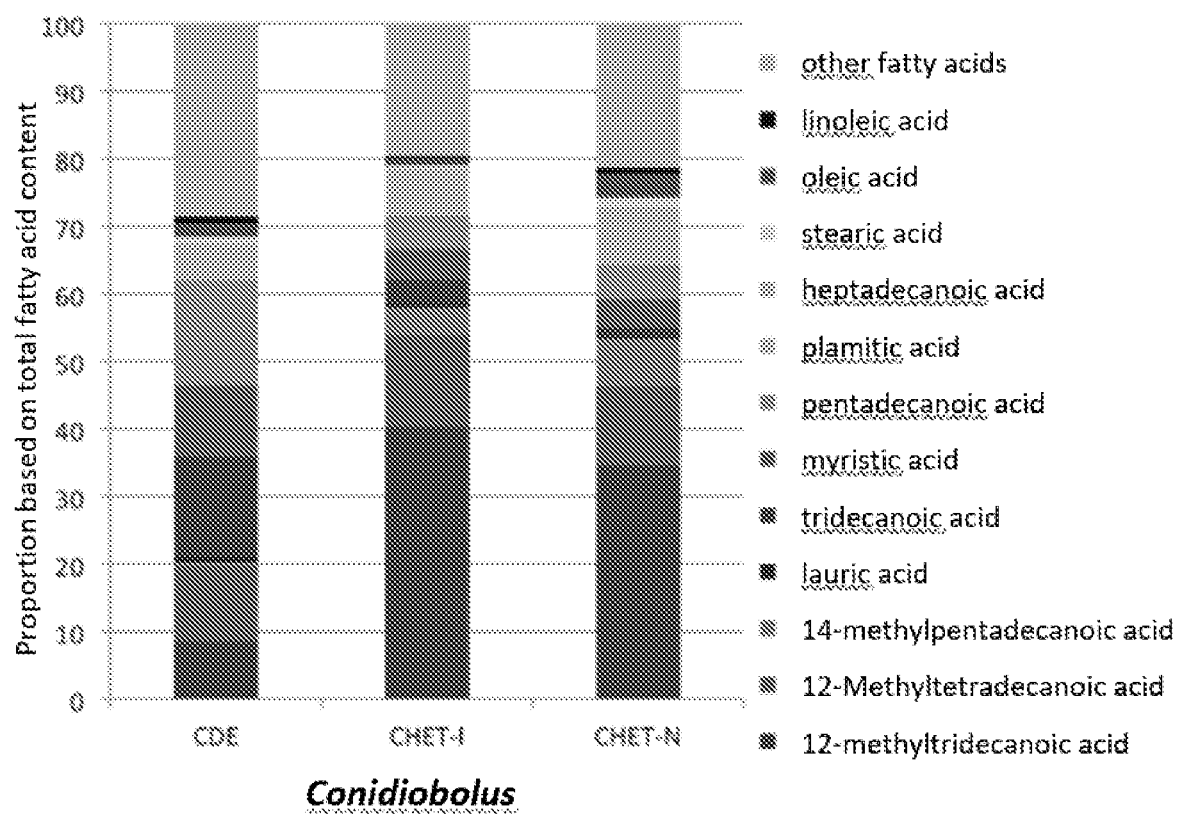
FIG. 1 shows the fractions of fatty acids based on the total fatty acid content of transerterified lipid extracts from different *Conidiobolus* strains.

A first object of the invention relates to a method for the production of branched aldehydes, preferably those comprising 12 to 18 carbon atoms and/or having a methyl branching, in particular 12-methyltridecanal, 12-methyltetradecanal, 14-methylpentadecanal, 16-methyloctadecanal or mixtures thereof, the method comprising the following steps:

(a) providing a culture of one or more fungi of the genus *Conidiobolus* and producing biomass containing branched carboxylic acids in free and/or bound form;

(b) extracting the biomass from step (a) to produce a first intermediate containing free and/or bound carboxylic acids;

(c) optionally hydrolyzing the bound carboxylic acids from the first intermediate chemically, enzymatically or microbially;

(d) treating the first intermediate with a reducing agent of a chemical nature to convert the free and/or bound carboxylic acids into the corresponding alcohols and optionally separating one or more alcohols from interfering by-components and producing the chemically produced second intermediate containing these alcohols as a mixture or in enriched form;

(e) treating the first intermediate with a reducing agent of a biological nature to convert the free and/or bound carboxylic acids into the corresponding aldehydes having the same number of carbon atoms as the free and/or bound carboxylic acids or into the corresponding aldehydes having a reduced number of carbon atoms by one compared to the free and/or bound carboxylic acids and producing the biologically produced second intermediate containing these aldehydes;

(f) treating the chemically produced second intermediate with an oxidizing agent of a chemical nature to convert the free and/or bound alcohols into the corresponding aldehydes; and optionally (g) removing interfering by-components from the fractions obtainable after steps (d) and/or (e) and/or (f).

Surprisingly, it was found that fungal genus *Conidiobolus* that has previously received little attention has a fatty acid pattern that makes this microorganism appear as a suitable starting material for the production of branched aldehydes in general and 12-methyltridecanal in particular. The final products can be obtained in sufficient yield and high purity by an optimized sequence of treatment with biological and/or chemical reducing agents and chemical oxidizing agents. The oxidized products are mixtures of branched aldehydes, which also contain linear species. These mixtures can be used directly, but it is also possible to obtain the highly desired product 12-methyltridecanal by targeted processing.

Organisms

The organisms which, due to the fatty acid spectrum they produce, serve as suitable bioreactors for the production of branched fatty acids of the desired chain length belong to a special genus of fungi, namely *Conidiobolus*, which mainly comprises saprobions that degrade dead plant material or live in the soil. The two preferred species *C. denaeosporus* and *C. heterosporus* are described in connection with decomposition of leaves of the Chinese elm (*Ulmus parvifolia*). Taxonomically, the two genera are classified as follows:

Kingdom: Fungi
Subphylum: Entomophthoromycotina
Order: Entomophthorales
Family: Ancylistaceae Overviews of these organisms were published by D. Tyrrell in the years 1968 to 1976: "The fatty acid composition of some Entomophthoraceae. II. the occurrence of branched-chain fatty acids in *Condiobolus denaesporus*" *Lipids* 3 (4), p. 368-372 (1968); "Fatty acid composition of some Entomophthoraceae. III" *Can J Microbiol* 17 (8), p. 1115-1118 (1971); and "The fatty acid composition of some Entomophthoraceae. IV. The occurrence of branched-chain fatty acids in *Conidiobolus* species". *Can J Microbiol* 22 (7), pp. 1058-1060 (1976).

Cultivation

Fungal mycelium/mycelia can be cultivated in a known manner using a suitable nutrient medium in solid or liquid culture. Agar plates produced with a nutrient solution of malt and yeast extract have proved their worth.

Extraction

After the cultures have formed a sufficient amount of biomass, the biomass, if necessary, is separated from the nutrient solution for example by centrifuging, filtration or other suitable separation methods. This is followed by extraction of carboxylic acids in their free or bound form. Solid cultures, such as those obtained after freeze-drying, can be extracted directly.

Further, insofar as reference has been made to extracts, they may be produced in a manner known per se, i.e. for example by aqueous, alcoholic or aqueous-alcoholic extraction of the cultures themselves or dry mass obtained therefrom. All conventional extraction methods are suitable, e.g. maceration, remaceration, digestion, motion maceration, vortex extraction, ultrasonic extraction, countercurrent extraction, percolation, repercolation, evacolation (extraction under reduced pressure), diacolation or solid-liquid extraction under continuous backflow. The percolation method is advantageous for large-scale use. Organic solvents, water (preferably hot water at a temperature above 80° C. and in particular above 95° C.) or mixtures of organic solvents and water, in particular low-molecular weight alcohols with more or less high water contents, may be used as solvents for carrying out the extractions.

Extraction with methanol, ethanol, pentane, hexane, heptane, acetone, propylene glycols, polyethylene glycols, ethyl acetate and mixtures thereof and their aqueous mixtures is particularly preferred. The extraction usually takes place at 20 to 100° C., preferably at 30 to 90° C., in particular at 60 to 80° C. In a preferred embodiment, extraction is carried out in an inert gas atmosphere to avoid oxidation of the active ingredients of the extract. This is particularly important for extractions at temperatures above 40° C. The durations of extraction are set by the skilled person depending on the starting material, the extraction method, the extraction temperature, the ratio of solvent to raw material and others.

After extraction, the raw extracts obtained may undergo further conventional steps, such as purification, concentration and/or discoloration. If desired, the extracts formed in this way can, for example, be subjected to a selective separation of individual undesirable ingredients. The extraction can occur to any degree of extraction, but is usually carried out until exhaustion. Typical yields (=amount of dry substance of the extract based on the amount of raw material used) in the extraction of the dry biomass are in the range of 3 to 15, in particular 6 to 10% by weight. The present invention encompasses the finding that the extraction conditions and the yields of the final extracts can be selected by the skilled person according to any desired field of application. These extracts, which usually contain active substance contents (=solids contents) in the range of 0.5 to 10% by weight, can be used as such, but it is also possible to completely remove the solvent by drying, especially by spray or freeze drying.

The extracts, which are hereinafter also referred to as the first intermediate, may be present as aqueous preparations and/or preparations dissolved in organic solvents as well as spray-dried or freeze-dried, anhydrous solids. In this context, aliphatic or branched alcohols with 1 to 6 carbon atoms (e.g. ethanol, 2-methoxy-2-methylpropane), ketones (e.g. acetone), halogenated hydrocarbons (e.g. chloroform or methylene chloride), lower esters or polyols (e.g. glycerol or glycols) are possible organic solvents.

Hydrolysis

If necessary, the extracts can be subjected to hydrolysis before the reduction to release the fraction of fatty acids bound as glyceride. The hydrolysis can occur chemically, but a biological alternative is preferable. This alternative can occur microbially, i.e. using living microorganisms, as well as enzymatically, since these hydrolyses are gentler and also offer regulatory advantages. Hydrolases from *Candida*, in particular *Candida rugosa* or *Candida cylindracea* are suitable for the biological alternative.

Reduction

After extraction, a first intermediate of a mixture of different linear and branched, saturated and unsaturated fatty acids, which can also be bound as glycerides, is obtained. Such a mixture may include, for example, the following representatives: tridecanoic acid, 12-methyltridecanoic acid, tetradecanoic acid, 12-methyltetradecanoic acid, pentadecanoic acid, 14-methylpentadecanoic acid, hexadecanoic acid, hexadecen(9)acid, 15-methylhexadecanoic acid, heptadecanoic acid, elaidic acid, oleic acid and arachidonic acid.

The mixture of fatty acids or fatty acid glycerides is now subjected to a reduction. Like hydrolysis, this can be done chemically, but preferably a biological alternative is chosen, as this then leads to a production method that is considered natural in the sense of European flavoring legislation. The preferred biological alternative can be carried out with enzymes as well as with cell lysates, cell extracts or whole cells that have the enzymatic activity required for the reduction. After this step, the reaction products can be extracted from the reaction mixture using extraction methods known to the skilled person. After removal of the extractant, the concentrate obtained can then be taken up in the desired concentration with the solvent of choice.

The chemical reduction of the mixture of fatty acids respectively fatty acid glycerides can be carried out with sodium borohydride, but lithium alanate should preferably be used. In the course of this conversion, the acid or ester functions are reduced to hydroxyl groups; the second, in this case chemical intermediate, thus completely or at least predominantly contains the corresponding alcohols of the linear and branched carboxylic acids. Within reaction times of about 3 hours, yields of 85% to 95% of the theoretical yield are achieved, which can be increased if the reduction is followed by another distillation step, for example a ball tube (bulb to bulb; Kugelrohr) distillation. Based on the amount of the particularly desired product 12-methytridecanol as a reduction product of 12-methytridecanoic acid, the yield is around 25 to 35% based on the total amount of reduction products. As a side reaction, the reduction also results in the saturation of unsaturated species contained in the mixture.

Reduction methods using hydrides belong to the standard reactions of a preparative organic chemists and represent textbook knowledge that therefore requires no further comprehensive explanation. The reduction is preferably carried out at temperatures in the range of 15 to 25° C., whereby, as expected, a temporary temperature increase occurs at the beginning of the reaction.

Oxidation

The second chemical intermediate serves as a starting material for the subsequent oxidation, during which the alcohols are converted into the corresponding aldehydes. TEMPO is preferably used as an oxidizing agent. TEMPO stands for 2,2,6,6-tetramethylpiperidinyloxyl.

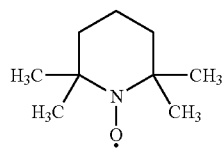

Although this radical is not thermodynamically stable, its comparatively high persistence is due to substituents that influence the service life through steric effects. The substituents are located in the vicinity of the radical electron, so that it has an average life of one minute in an oxygen-free solution. The use of TEMPO together with a suitable co-oxidant for the two-phase oxidation of alcohols is described by Anelli et al. in *J Organic Chemistry*. 52, p. 2559-2562 (1987) ("Anelli oxidation") and used for example in *Organic Syntheses, Coll. Vol.* 8, p. 367 (1993); *Vol.* 69 p. 212 (1990).

For the purposes of this invention, it has proven advantageous to use TEMPO in combination with two co-oxidants, namely an alkali bromide and an alkali hypochlorite. A combination of potassium bromide and sodium hypochlorite is preferred here. A molar ratio of TEMPO, alkali bromide and alkali hypochlorite of about 1:(2 to 10):(10 to 40), particularly about 1:(2 to 10):(10 to 40) and more particularly of about 1:(4 to 8):(15 to 30) has proven its worth. Since the reaction is highly exothermic, it is recommended to keep the reaction temperature in the range of about −5 to +10° C.

Under these conditions, yields in the range of 85 to 97% based on the alcohols used are obtained. In relation to the preferred target product 12-methyltridecanal the yield is 30 to 35%, whereby a purity of approx. 95% is achieved.

Also in the case of the oxidation, purity can be further improved by subjecting the products to a distillation step, such as a ball tube (Kugelrohr) distillation or by means of a split tube (Spaltrohr).

When selecting an enzymatic process for the biological reduction, enzymes such as commercially available aldehyde dehydrogenases (ALDH, EC 1.2.1.x) and carboxylic acid reductases, e.g. from *Norcardia* sp. (Aimin He, Tao Li, Lacy Daniels, Ian Fotheringham, John P. N. Rosazza *Appl Environ Microbiol*. 2004 March; 70(3): 18744881) and/or *Mycobacterium marinum* (M. Kalim Akhtar, Nicholas J. Turner, Patrik R. Jones *Proc Natl Acad Sci USA*. 2013 Jan. 2; 110(1): 87-92), can be used. Carboxylic acid reductases can be obtained by homologous expression in *Nocardia* sp. or *Mycobacterium* sp., in particular *Nocardia iowensis*, as well as heterologously by recombinant expression in suitable host organisms in particular *E. coli*, but preferably also by cultivation of *Nocardia iowensis*, which as so-called wild-type strain also expresses the enzymes. For the actual conversion it is irrelevant whether the enzymes are present in purified form, are only partially concentrated, or are present in a cell raw extract or in native or recombinant cells.

INDUSTRIAL APPLICABILITY

A further object of the invention concerns a concentrate of methyl-branched aldehydes having 12 to 18 carbon atoms, obtainable by the method described above, which concentrate can contain the methyl-branched aldehydes in amounts of 10 to 100, preferably 25 to 95 and in particular about 40 to about 60% by weight. The concentrates can be obtained directly on the basis of the chemically formed second intermediate (f), the biologically formed second intermediate (e) or the completely or partially purified products (g) by suitable, preferably gentle drying methods, such as spray drying or freeze drying. The difference to 100% by weight may be due to carriers and/or other flavoring substances. Alternatively, concentrated aqueous solutions can also be sold.

A final object of the present invention concerns the use of the concentrates or alternatively the products directly obtained by the process as described above as flavoring components, in particular as flavoring components for foodstuffs, in order to give them a beef flavor.

EXAMPLES

Example 1

Cultivation of Fungal Strains

Used Fungal Strains

Table 1 below gives an overview of the fungi examined, their exact designation, number of the strain collection (CBS number), the isolation substrate and the isolation site.

TABLE 1

Fungi assessed

| Organism | CBS number | Isolation substrate and site | Abbreviation |
|---|---|---|---|
| *Conidiobolus denaeosporus* | 137.57 | decomposed leaves of *Ulmus parvi-folia*, (US) | CDE |
| *Conidiobolus heterosporus* | 333.74 | agricultural soil (NL) | CHET-N |
| *Conidiobolus heterosporus* | 138.57 | Forest leaf litter (US) | CHET-U |

Cultivation on Solid Medium

The fungal strains were cultivated on malt extract agar plates. To produce the plates, the media components were weighed (Table 2), filled up with distilled water to 1 litre and autoclaved (120° C., 20 min). A 1 cm² mycelium-covered piece of agar from the vital peripheral area of a plated culture was placed in the middle of the agar plates, the petri dishes were sealed with parafilm and then incubated with or preferably without light at 24° C. in the incubator. After about 5 days (CHET-N) and 14 days (CHET-U and CDE), pre-cultures were inoculated from the plates that were about three-quarters overgrown. In parallel, further agar plates for the next pre-cultures were inoculated according to the same principle. Table 2 shows the composition of the malt extract-yeast extract-agar for the cultivation of *Conidiobolus* strains:

TABLE 2

| Composition agar | |
|---|---|
| Medium component | Concentration [g L$^{-1}$] |
| Agar | 15 |
| Malt extract | 30 |
| Yeast extract | 3 |

For the submerged pre-cultures a complex nutrient medium was used, which is shown in Table 3:

TABLE 3

| Composition of the standard complex medium | |
|---|---|
| Medium component | Concentration [g L$^{-1}$] |
| Malt extract | 30 |
| Yeast extract | 3 |

For cultivation in submerged culture, a 1 cm² agar piece of the outer mycelium was transferred under sterile conditions to a 250 mL Erlenmeyer flask filled with 100 mL culture medium and treated with an ultraturrax dispersing rod (30 s, 9,800 rpm). The pre-cultures were incubated at 24° C. in an incubator (Multitron, Infors, Einsbach; 24° C., 150 rpm, deflection 25 mm) with no light.

Main culture: For cultivation of the main cultures, the pre-culture was treated under sterile conditions with an ultraturrax dispersing rod (30 s, 9,800 rpm). 20 mL of this suspension was added to 200 mL fresh culture medium in a 500 mL Erlenmeyer flask. Cultivation took place at 24° C. with exclusion of light in an incubation shaker (24° C., 150 rpm, deflection 25 mm).

Example 2

Cell Harvesting and Fat Extraction

The main culture was filtered through a filter paper (range of retention 8-12 μm) at the end of the cultivation period. The residue was mixed with about 200 mL 4 M HCl, heated to boiling point and digested for 30 min in the boiling heat. The solution was then filtered through a pleated filter while still hot and washed with hot water until the wash water was neutral. After drying for 1-2 h in a drying cabinet (100° C.), the filter paper was extracted for 4 h with petroleum gasoline (boiling range 40-60° C.) using a Soxhlet apparatus. After removing the solvent with a rotary evaporator, the fat content was determined gravimetrically.

Alternatively, the main culture can be filtered through a filter paper (retention range 8-12 μm) at the end of the cultivation period and then lyophilized. The lyophilisate was then grindet with purified sand, mixed 3 times with approx. 75 ml hexane each and extracted with 40-120 bar pressure in a SpeedExtractor from Büchi. After removing the solvent with a rotary evaporator, the fat content was determined gravimetrically.

Figure 2:
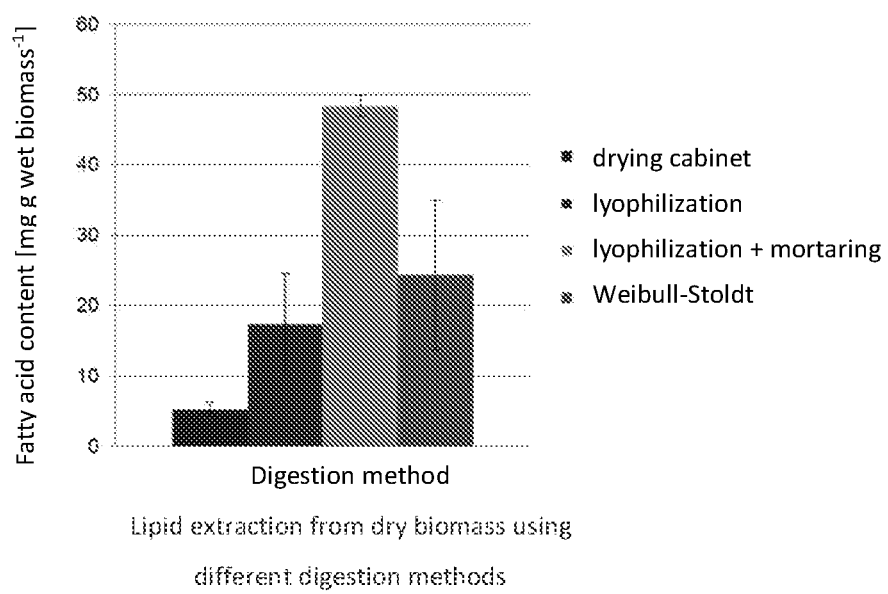
FIG. 2 shows a fat content based on digestion method.

Various approaches were investigated to identify the most suitable processing method for the fermentatively produced biomass. Lyophilization with subsequent fine-grinding was identified as the most suitable method. FIG. 1 shows the fractions of fatty acids based on the total fatty acid content of the transesterified lipid extracts from different *Conidiobolus* strains; all fatty acids were determined by gas chromatography as fatty acid methyl esters. The fat content depending on the digestion method is shown in FIG. 2.

Example 3

Enzymatic Hydrolysis Using Lipase

Figure 3:
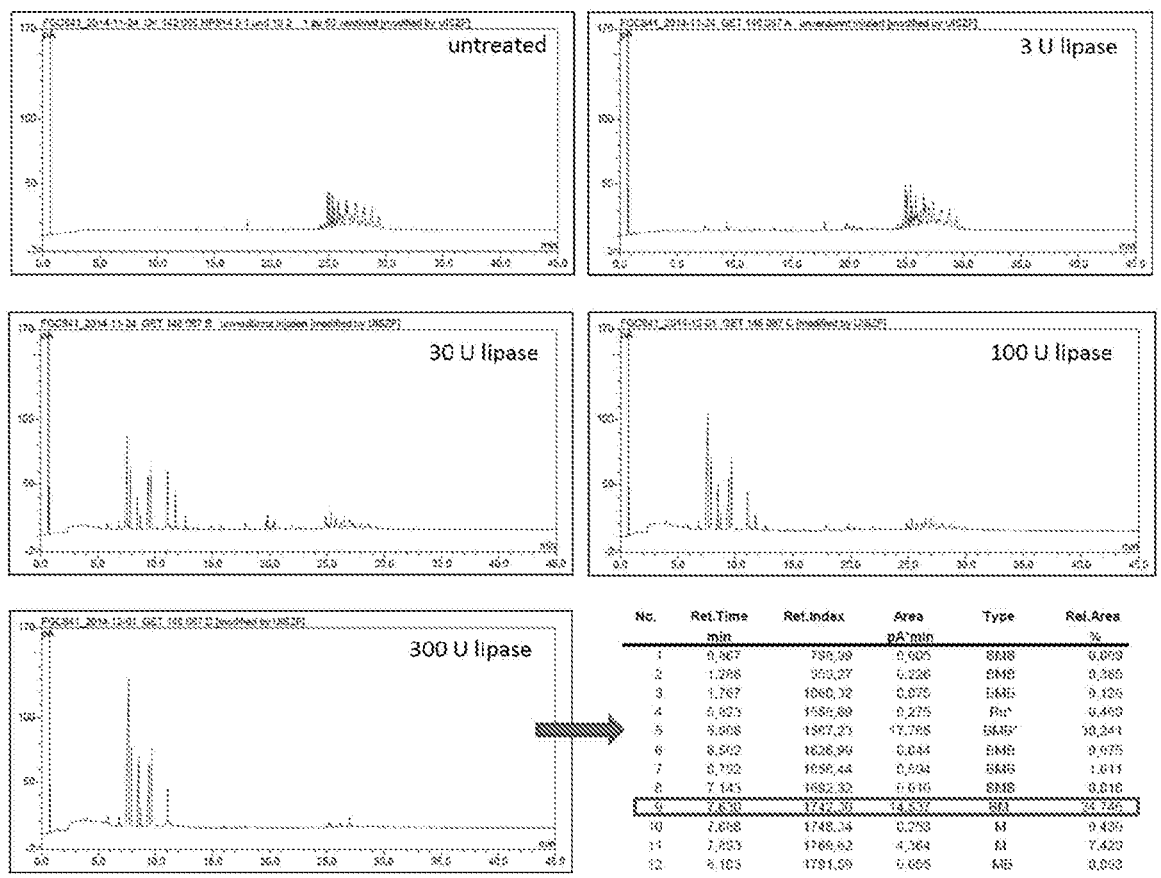
FIG. 3 shows a fatty acid distribution determined by gas chromatography.

About 50 mg of the lipid extract obtained after extraction of the biomass was mixed with 10-100 μl of a lipase enzyme solution of "Lipase AY" of Amano (from *Candida cylindracea*) having different concentrations, 100-190 μl phosphate buffer (200 mM, pH 7.6) and 100 μl water and incubated overnight in a thermoblock (Eppendorf) (45° C., 800 rpm). To prepare the buffer, a 0.2 M Na$_2$HPO$_4$ solution was prepared and mixed with a 0.2 M KH$_2$PO$_4$ solution, so that a pH of 7.0 was obtained. The concentration ratios examined are shown in Table 4. Subsequently, the samples were shaken out with 2 mL hexane and the upper (organic) phase was filled into glass vials to determine the fatty acid distribution by GC (without previous methylation) (FIG. 3). No free fatty acids were present in the untreated fat fraction. By hydrolysis with the lipase fatty acids were released, strongly dependent on the amount of enzyme used (with 3 U enzyme only very little is released, but with 30 U substantially more). A total of 14% 12-methyltridecanoic acid was found. In a repetition of the experiments with 100 U and 300 U enzymes a total of 25% by weight of 12-methyltridecanoic acid was determined.

TABLE 4

| Reaction preparations for hydrolysis of the fat extract | | | | |
|---|---|---|---|---|
| | A | B | C | D |
| Fat fraction | 50 mg | 50.4 mg | 51 mg | 51.3 mg |
| Lipase solution (10 mg/ml) | 10 μl | 100 μl | | |
| Lipase solution (100 mg/ml) | | | 20 μl | 100 μl |
| Amount of lipase (U Lipase) | 3 | 30 | 100 | 300 |
| Phosphate buffer (200 mM), pH 7 | 190 μl | 100 μl | 180 μl | 100 μl |
| H$_2$O | 100 μl | 100 μl | 100 μl | 100 μl |

Example 4

Conversion of 12-Methyltridecanoic Acid with α-Dioxygenase

The production of α-Dioxygenase was carried out in accordance with literature references based on the method described in patent application WO 2012/025629 A1. 1 μL of the plasmid was pipetted to competent *Escherichia coli* cells [BL21(DE3), Novagen] for cell transformation. After a cooling phase (30 min on ice) the samples were heated for 2 min in a water bath (42° C.) and cooled again. For cultivation 150 μL LB-Kanamycin medium (Table 5) was added and incubated for 1 h (37° C., 200 rpm, deflection 25 mm). The cell suspension was applied to pre-dried and acclimatized LB-kanamycin agar plates and incubated at 37° C. overnight.

TABLE 5

| Composition of the LB-Kanamycin medium | |
|---|---|
| Amount | Components |
| 10 g L$^{-1}$ | Trypton |
| 5 g L$^{-1}$ | Yeast extract |
| 10 g L$^{-1}$ | NaCl |
| 25 mg L$^{-1}$ | Kanamycin (not autoclaved but added sterile filtered) |

For the conversions using α-dioxygenase, this enzyme was expressed in *E. coli* cells [BL21(DE3)] on LB medium according to WO 2012 025629 A1. A 0.5 cm long smear was taken from the bacterial lawn using an inoculation loop, transferred to 3 mL LB kanamycin medium and incubated up to an $OD_{600}$ between 0.5-0.8 in a shaker (37° C., 150 rpm, deflection 25 mm). Isopropyl-D-thiogalactopyranoside (IPTG) was added (0.5 mM) and the sample incubated for another 16-18 h in the shaker (24° C., 150 rpm, deflection 25 mm). The sample was centrifuged (4,000 rpm, 3,724×g, 10 min, 4° C.), the supernatant discarded and the cell pellet frozen (−20° C.).

Frozen cell pellets produced as described above were taken up in phosphate puffer (200 mM, pH 7.6), washed in the same buffer, centrifuged and resuspended in 2 mL phosphate buffer to which 0.5% glucose monohydrate was added. To 1 mL of the cell suspension 50 μL 12-methyltridecanoic acid (7.5 mg $mL^{-1}$ in DMSO) was added. The sample was incubated for 1 h at 37° C. (150 rpm, deflection 25 mm) and then extracted with 1 mL heptane. After drying the organic phase over sodium sulphate the sample was examined by gas chromatography.

Example 5

Conversion of the Lipid Extract with α-Dioxygenase

The conversion was carried out in comparable manner as Example 4, in which a standard solution with 12-methyltridecanoic acid was used. To 2 ml of the *E. coli* cells resuspended in phosphate buffer, 10 μl of the fat extract of the fungal culture from Example 2 was added, extracted as in Example 4 and then examined by gas chromatography.

Example 6

Simultaneous Conversion with Lipase and with α-Dioxygenase 145 mg of a lipid extract of *C. denaeosporus* from Example 2 was weighed into a 10 mL vial and mixed with 200 μl lipase enzyme solution from Example 3, 200 μL phosphate buffer (200 mM, pH 7.6) and 200 μL water. 200 mg of the *E. coli* cells producing α-dioxygenase from Example 4 were washed with phosphate buffer (200 mM; pH 7.6) and resuspended in 4 mL phosphate buffer, which contained 0.5% glucose monohydrate, and added to the prepared 10 mL vial. The reaction preparation was incubated overnight (22 h, 24° C., 150 rpm, deflection 25 mm). The converted fat was extracted 3 times with 2 mL heptane each and the organic phases were combined. After dilution (1:50) the samples were analyzed by gas chromatography.

Example 7

Conversion with Aldehyde Dehydrogenase (ALDH)

Figure 6:
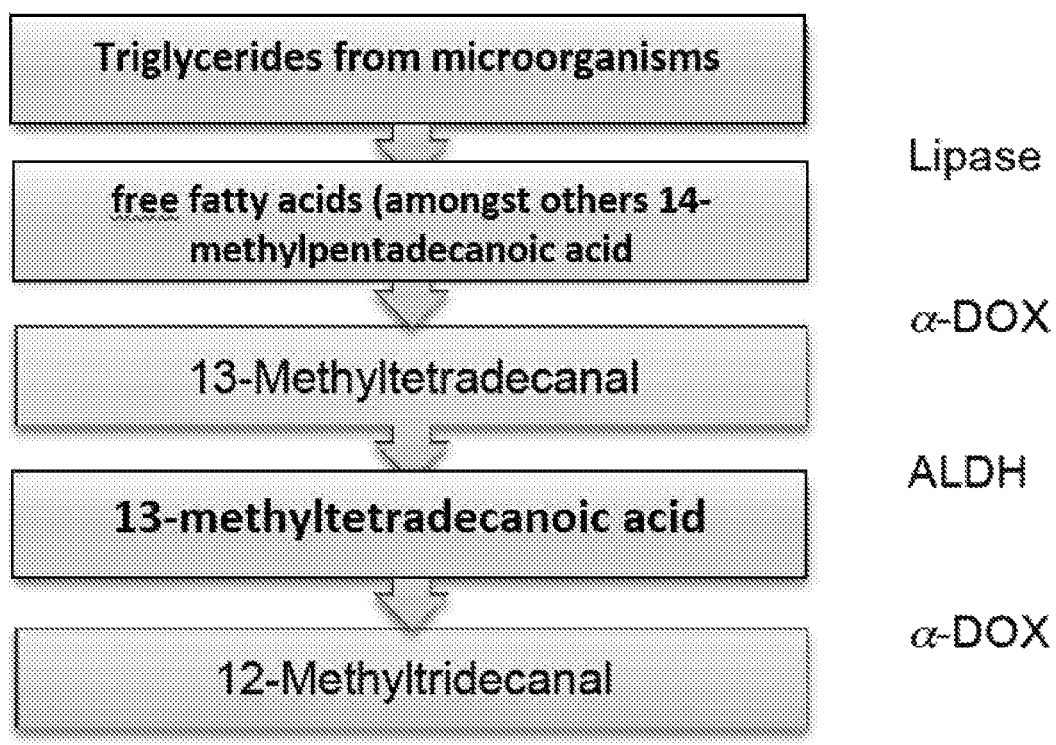
FIG. 6 shows a schematic diagram showing production of 12-methyltridecanal.

For conversion with aldehyde dehydrogenase (ALDH from *Saccharomyces cerevisiae*, 10.5 U $mg^{-1}$ protein), about 15 mg 12-methyltridecanoic acid was emulsified with 500 μL Triton-X-100 solution (2.2 g $L^{-1}$). The conversion was carried out in accordance with *Sigma Quality Control Test*1 based on Bostian et al., (1978) *Biochemical Journal* 173, 773-786. After enzyme addition the samples were incubated in a shaker (30 min, 24° C., 150 rpm, deflection 25 mm) and then shaken out twice with 1 mL pentane/diethyl ether (1:1.12, v/v) each. Prior to gas chromatographic analysis, the sample was mixed with 50 μL internal standard (750 mg $L^{-1}$ thymol). Alternatively, a reduction with an α-dioxygenase was carried out in a further experiment as shown in FIG. 6.

Example 8

Reduction of 12-methlytridecanoic Acid with Carboxylic Acid Reductases

Protein expression of Nsp-CAR and MmFad9 was performed in recombinant *E. coli* BL21 (DE3) cells. For this, 50 ml LB medium was inoculated with 30 μg kanamycin/ml from a master stock and incubated at 37° C. and 130 rpm until an $OD_{600}$ of about 0.6-0.8 was achieved. When this value was reached, 1 mM IPTG was added for induction and the cultures were continued to grow overnight at room temperature. The biomass thus obtained was centrifuged at 10,000 rpm for 10 minutes and the cell pellet was stored at −20° C. until further use.

To recover protein, the pellets stored at −20'C were thawed and resuspended with 4 ml B-PER reagent per g pellet. After adding 50 μg lysozyme/ml and 2.5 U DNase/ml, the samples were incubated for 15 minutes at room temperature, then centrifuged for 10 minutes at 10,000 rpm and 4° C. to obtain the total protein extract. After subsequent purification of the enzymes using HisPur Ni-NTA columns, the protein concentrations of the purified enzymes were determined according to Bradford (9.92 mg/ml for Nsp-CAR and 26.43 mg/ml for MmFad9).

Figure 4:
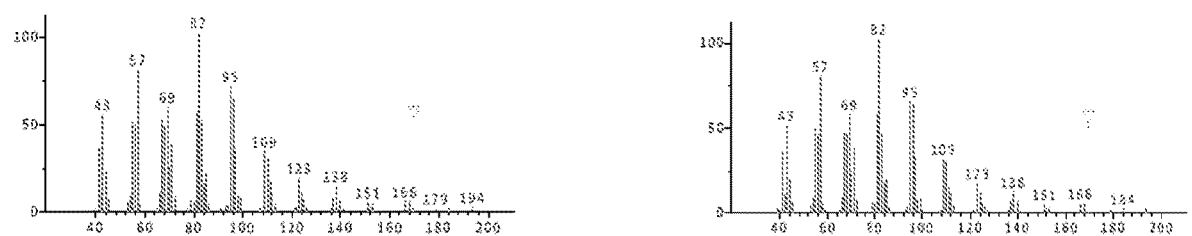
FIG. 4 shows a mass spectra of standard of 12-methyltridecanal (right part) and after reduction with Nsp-CAR (left part)

The enzyme assay was performed using 50 mM Tris-HCl buffer (pH=7.5), 20 mM substrate, 10 mM ATP, 10 mM NADPH, 100 mM $MgCl_2$ and 1 mg of the purified enzyme so that the total volume was 1.1 ml. After an incubation period of 24 h at room temperature, the aqueous mixture was shaken out 3 times each with 1:1 hexane and the upper, organic phase was transferred to a GC vial. The results obtained are summarized in Table 6. FIG. 4 shows the mass spectra of the standard of 12-methyltridecanal (right part) and after reduction with Nsp-CAR (left part).

[1]FIG. 4: left: Mass spectrum of 12-methyltridecanal generated from homologous acid by reduction using CAR; right: mass spectrum of the standard of 12-methytridecanal

TABLE 6

12-methyltridecanoic acid and 12-methyltridecanal contents of the enzymatic conversions

|  | 12-Methyltridecanal [μg/ml] | | | 12-Methyltridecanoic acid [μg/ml] | | |
| --- | --- | --- | --- | --- | --- | --- |
|  | Rep. 1 | Rep. 2 | Rep. 3 | Rep. 1 | Rep. 2 | Rep. 3 |
| MmFad9; 1st extraction | 1.38 | 1.755 | 1.98 | 3105 | 3382.5 | 3333 |
| MmFad9; 2nd extraction | 0.2125 | 0.4 | 0.3625 | 153.75 | 192.5 | 197.5 |
| MmFad9; 3rd extraction | — | — | — | 12 | 20 | 22 |
| Nsp-CAR; 1st extraction | 1.475 | 1.7125 | 1.8625 | 2850 | 2975 | 2975 |
| Nsp-CAR; 2nd extraction | 0.3 | 0.475 | 0.3 | 153.75 | 162.5 | 160 |
| Nsp-CAR; 3rd extraction | — | — | — | 20 | 22 | 23 |

Example 9

Reduction of 12-Methyltridecanoic Acid in a Biotransformation (with Living *E. coli* BL21 Cells that can Express Either Nsp-CAR or MmFad9)

By the fact that Akhtar et al. (P Natl Acad Sci USA 2013; 110: 87-92) described that the catalytic activity of reductases can be positively influenced by the presence of the protein BsSfp, a corresponding *E. coli* strain was grown in parallel in LB medium at 37° C. and 150 rpm overnight and added to the biotransformation preparation.

*E. coli* cells expressing reductase and the auxiliary enzyme were initially grown to cultures so that they reached an OD of about 2. The biotransformation preparations were then prepared in such a way that for each preparation each reductase was present once with respectively without auxiliary protein as well as a preparation each as a positive control, in which 100 µl of a benzoic acid solution was added to each reductase. In addition to the volumes of about 1 ml each, which were required for the expressing *E. coli* strains, 5 µl IPTG (final concentration in the preparation 1 mM), 100 µl of an ethanolic 12-methyltridecanoic acid solution (final concentration in the preparation 2 mM) and about 3 to 4 ml fresh LB medium were added to each preparation, so that after completion the preparations had an OD of about 0.5 in a final volume of 5 ml. The preparations thus prepared were cultivated in duplicates for 24 h at room temperature at a shake frequency of 150 rpm. Subsequently, each preparation was extracted 2 times with hexane in a ratio of 1:1. The results from the biotransformations are listed in Table 7.

TABLE 7

Results of biotransformations for the formation of 12-methyltridecanal

| Enzyme | 12-Methyltridecanal µg/ml | | 12-Methyltridecanoic acid µg/ml | | 12-Methyltridecanol µg/ml | |
|---|---|---|---|---|---|---|
| Nsp-CAR | 0.77 | 0.75 | 5.97 | 5.80 | 24.7 | 22.5 |
| Nsp-CAR + BsSfp | 0.58 | 0.51 | 13.09 | 12.68 | 11.1 | 10.5 |
| MmFad9 | 0.31 | 0.31 | 58.32 | 63.51 | 2.5 | 2.8 |
| MmFad9 + BsSfp | 0.28 | 0.33 | 62.33 | 64.93 | 0.9 | 0.9 |

Example 10

Hydrolysis of a Fat Fraction of *Conidiobolus heterosporus* Using Lipase and Subsequent Conversion with the Carboxylic Acid Reductases MmFad9 Respectively Nsp-CAR to Form 12-methyltridecanal Hydrolysis was performed with pooled lipid extracts, as they can be obtained following the description of Example 2, in accordance with the description of Example 3. 150 mg of the thus hydrolyzed fat extract were mixed with 1010 µl of a reaction mixture as shown in Table 8. MS/MS analyses, shown in FIG. 5, showed that 12-methyltridecanal could be identified with both hydrolyzed and non-hydrolyzed fat extracts.

Figure 5:
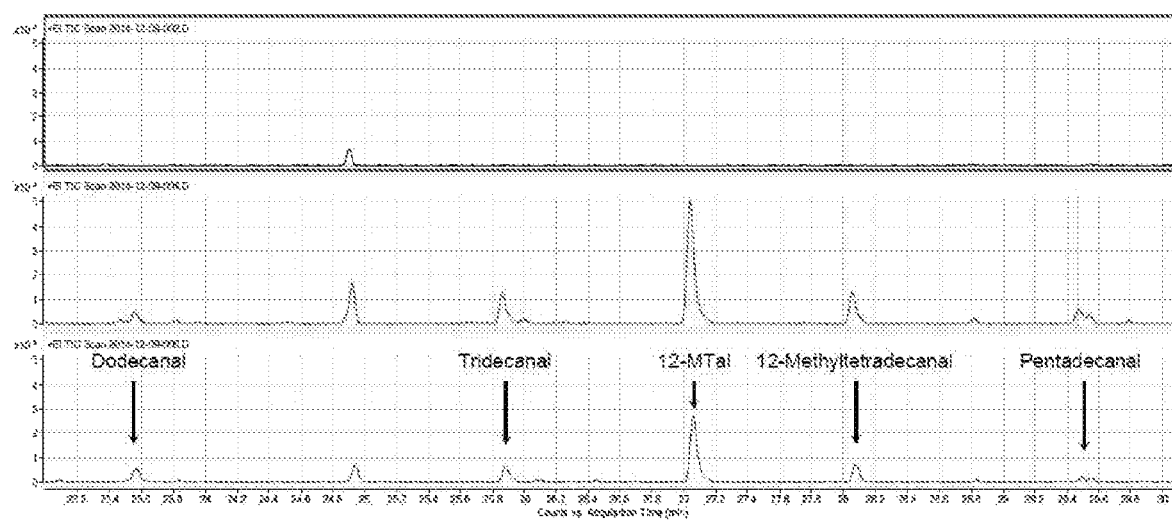
FIG. 5 shows an MS/MS chromatogram (TIC, scan in Q1) of a blank value (heat-inactivated CAR) of the enzymatic conversion of the lipid extract (top); reaction of the lipid extract without addition of lipase (middle); and conversion of the lipid extract with lipase and CAR (bottom)

[2] FIG. 5: top: MS/MS chromatogram (TIC, scan in Q1) of the blank value (heat-inactivated CAR) of the enzymatic conversion of the lipid extract; center: Reaction of the lipid extract without addition of lipase; bottom: Conversion of the lipid extract with lipase and CAR

TABLE 8

Composition of the reaction mixture for reducing hydrolyzed fat extract

| Substance | Amount used |
|---|---|
| CAR protein solution from Example 8 | 900 µL |
| ATP disodium salt | 1 mM |
| NADPH tetranodium salt | 1 mM |
| MgCl2 * 6 H2O | 10 mM |
| final volume | 1.010 ml |

Example 11

Reduction of a Fat Extract of *Conidiobolus heterosporus* with Living Cells of *Nocardia iowensis* for the Production of 12-methyltridecanal 1 mL was taken from a cryopreserve of *Nocardia iowensis* (DSM 45197) and transferred to a 100 ml flask containing 10 ml LB medium and 0.05% Tween 80. The flask was cultivated for approx. 72 h at 28° C. and 130 rpm with a shaking amplitude of 50 mm. Afterwards, 1 ml was taken from the well-grown culture and transferred to a 100 ml Erlenmeyer flask with also 10 ml of the same fresh medium. Analogous to T. Li et. al. (*J Bacteriol. June* 1997; 179(11): 3482-3487) 5 mg benzoic acid/ml was added for induction and the flask was incubated for another 24 h at 28° C. and 130 rpm. Subsequently, biocatalyses were carried out according to the compilation of Table 9. After the induction phase, the substrate was added and the preparations were incubated for another 24 h at 28° C. and 150 rpm. The samples were then extracted 2:1 with hexane, the organic phase was transferred to a sample container and examined by gas chromatography for 12-methyltridecanoic acid and 12-methyltridecanal. The results are summarized in Table 9:

TABLE 9

Experimental results from the biocatalysis tests

| Substrate | 12-Methyl-tridecanal [µg/ml] | 12-Methyl-tridecanoic acid [µg/ml] |
|---|---|---|
| Lipase-hydrolyzed fat fraction of *C. heteropsorus* (from Example 3) | 0.39 | 8.4 |
| Fat fraction of *C. heterosporus* dissolved in DMSO without prior hydrolysis (from Example 2) | — | 6.9 |
| 12-Methyltridecanoic acid | — | 107.0 |
| Fat fraction of *C. heterosporus* without prior hydrolysis | 0.60 | 42.7 |

Example 12

Chemical Conversion of Fat Extracts from *C. Heterosporus* to 12-methltridecanal The previously obtained fat extracts were divided into two qualities: those with a fat content of less than 1 g/L and those with higher contents. The conversion occurred in two steps, first as reduction with the help of lithium alanate and then as oxidation with TEMPO/KBr/NaOCl. The reaction conditions are given in Table 10 below:

TABLE 10

Reaction conditions*

| Preparation | Reaction conditions | Yield [g] | Yield [%] | Purity by GC-MS [%] direct | after ball tube (Kugelrohr) distillation |
|---|---|---|---|---|---|
| 078 | LiAlH4 (0.7 eq.) RT, 3 h | 17.3 | 89 | 33.1 | 37.4 |
| 083 | LiAlH4 (0.7 eq.) RT, 3 h | 10.7 | 93 | 30.3 | 37.2 |
| 081 | KBr (0.28 eq.), TEMPO (0.067 eq.), NaClO (1.2 eq.), 0° C., 4 h | 16.0 | 87 | 36.9 | 44.8 |
| 085 | KBr (0.30 eq.), TEMPO (0.073 eq.), NaClO (1.2 eq.), 0° C., 3 h | | | | 34.2 |

*078: 27.4 g of <1 g/L, 083: 17.8 g of >1 g/L, 081: <1, 085: >1

Figure 7A:
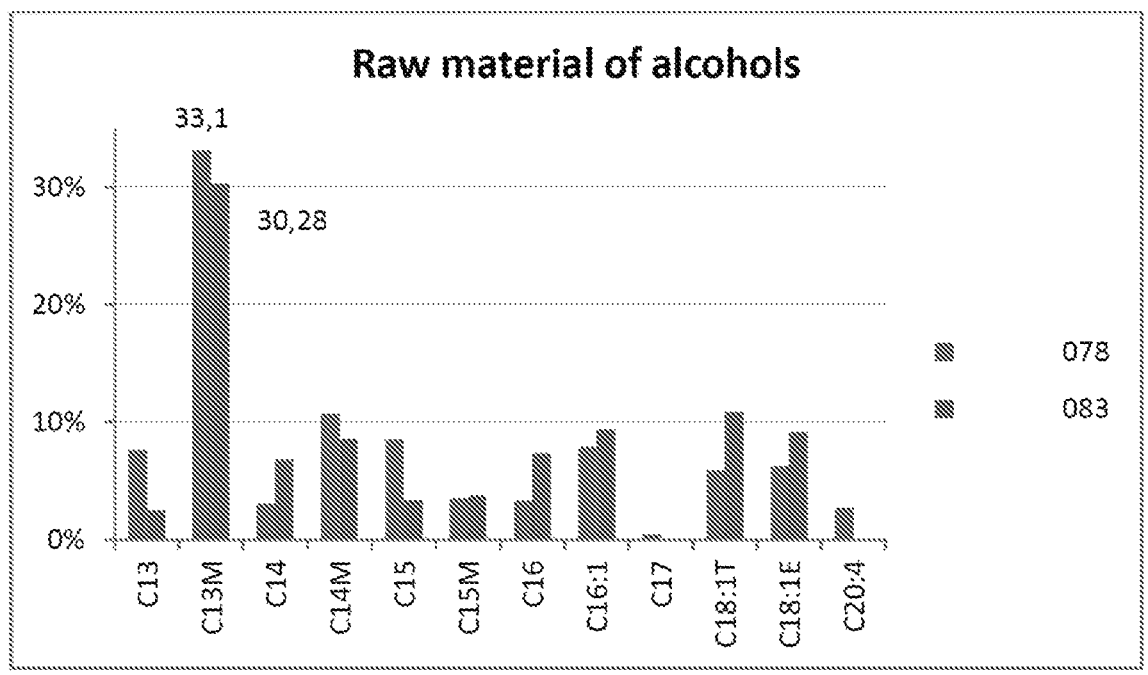
FIG. 7A shows the composition of the resulting alcohols before and after ball tube distillation for the two preparations designated 078 (<1 g/L) and 083 (<1 g/L) (raw material of alcohol)
Figure 7B:
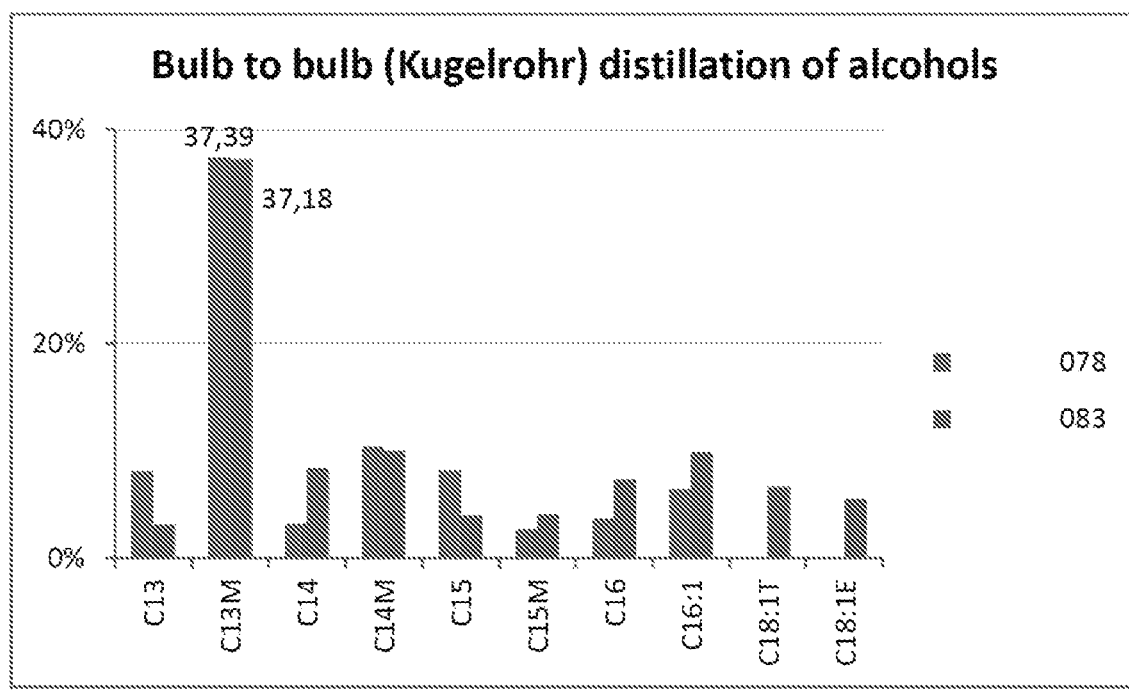
FIG. 7B shows the composition of the resulting alcohols before and after ball tube distillation for the two preparations designated 078 (<1 g/L) and 083 (<1 g/L) (bulb to bulb distillation of alcohols)

The reduction with lithium alanate yielded 89% for the <1 g/L experiment and 93% for the >1 g/L experiment (in each case after ball tube distillation) based on the content of 12-methyltridecanoic acid or the corresponding glycerides. The proportion of double bonds was reduced from 22% to 6% and from 29% to 22%, respectively. FIGS. 7A and 7B show the composition of the resulting alcohols before and after ball tube distillation for the two preparations designated 078 (<1 g/L) and 083 (>1 g/L).

Figure 7C:
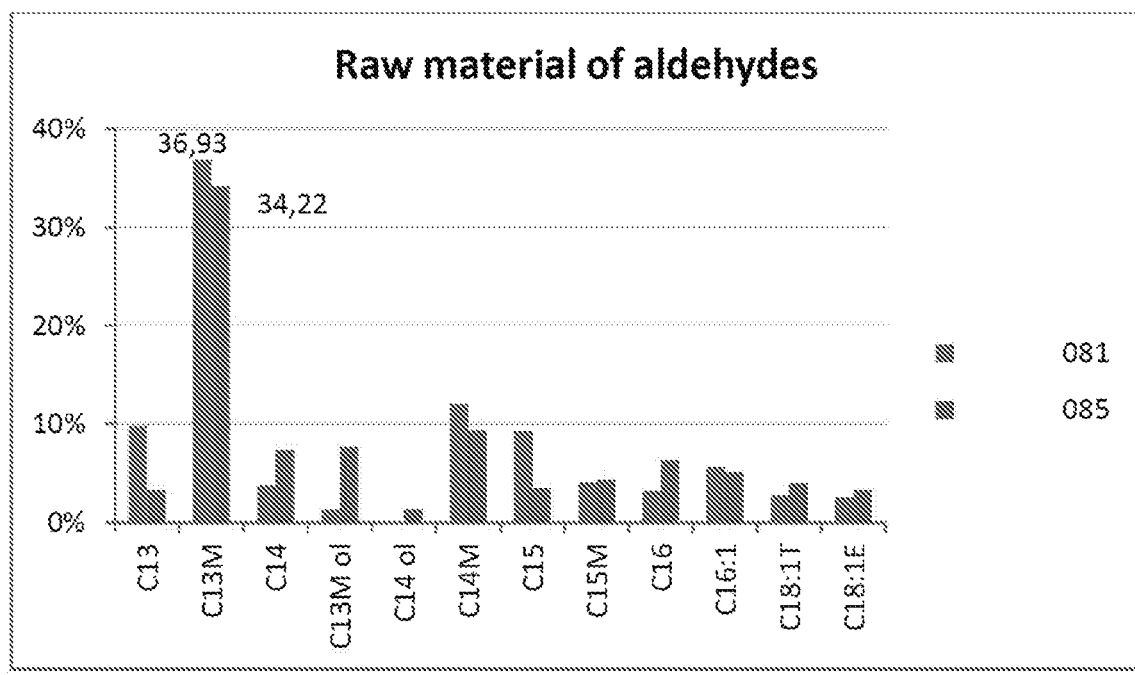
FIG. 7C shows the composition of the resulting aldehydes the two preparations of FIG. 7A and FIG. 7B after subsequent oxidation for TEMPO.

The subsequent oxidation with TEMPO gave an aldehyde yield of 97% (081) for the case <1 g/L and 94% for the case >1 g/L (085) based on the content of 12-methyltridecanoic acid respectively the corresponding glycerides (in each case before ball tube distillation). The results are shown in FIG. 7C.

Figure 8A:
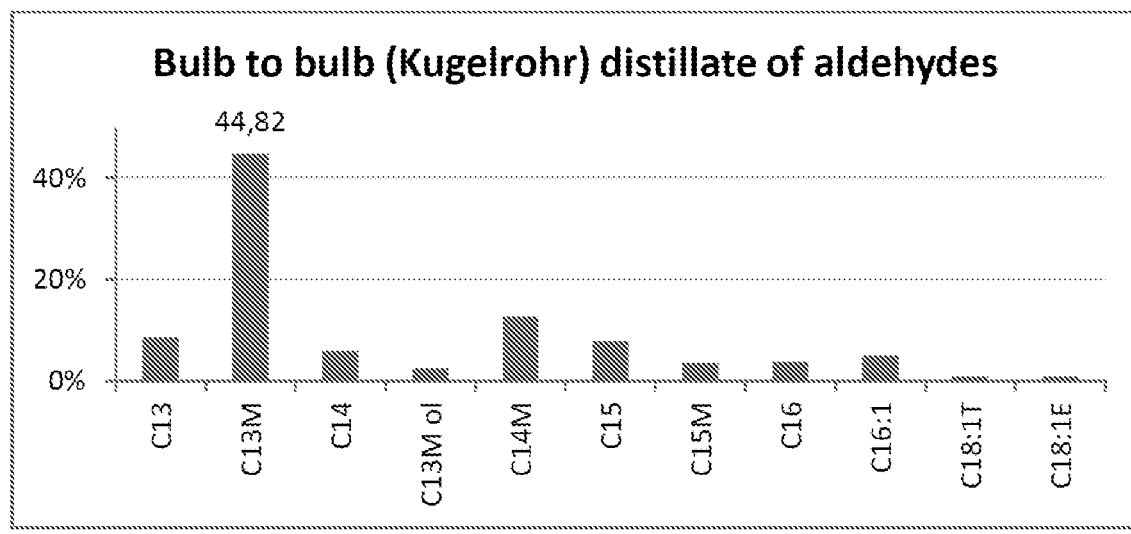
FIG. 8A shows the results of aldehyde fractions that were pooled and distilled in a ball tube.
Figure 8B:
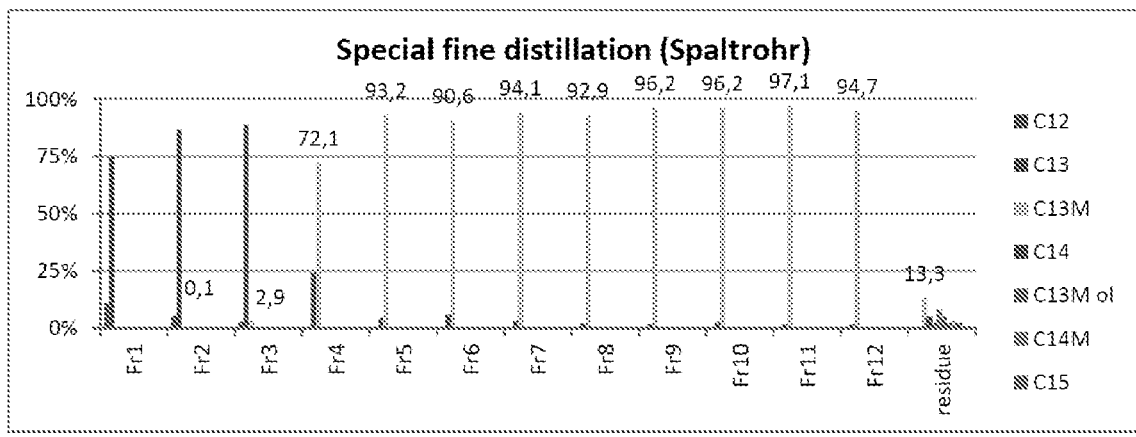
FIG. 8B shows the result of a distillate subjected to further purification in a split tube.

The obtained aldehyde fractions (#081 and #085) were pooled and again distilled in the ball tube. 19.6 g (GC purity 44.8%) corresponding to a yield of 77% based on the amount of 12-methyltridecanoic acid or the corresponding glycerides were determined. The results are shown in FIG. 8A. The resulting distillate was subjected to further purification in the split tube (Spaltrohr) (72-83° C., 0.5 mbar). Various fractions with purities of more than 95% were obtained (FIG. 8B). The compositions are shown in Table 11.

TABLE 11

Purity of the fractions from split tube distillation

| | Purity 12-MTD (GC) | Amount [g] |
|---|---|---|
| 085 KD1 Fr1 | 44.8% | 19.6 |
| Split tube Fr1 | — | 1.1 |
| Split tube Fr2 | 0.1% | 0.1 |
| Split tube Fr3 | 2.9% | 1.1 |
| Split tube Fr4 | 72.1% | 1.1 |
| Split tube Fr5 | 93.2% | 1.1 |
| Split tube Fr6 | 90.6% | 0.2 |
| Split tube Fr7 | 94.1% | 0.4 |
| Split tube Fr8 | 92.9% | 0.3 |
| Split tube Fr9 | 96.2% | 1.0 |
| Split tube Fr10 | 96.2% | 0.4 |
| Split tube Fr11 | 97.1% | 0.5 |
| Split tube Fr12 | 94.7% | 0.2 |
| Residue | 13.3% | 12.2 |

The total yield of oxidation of the two pooled qualities from fractions 5 to 12 (4.1 g, purity 94.7%) was 38% based on the alcohol mixtures (17 g with 37.4% purity and 10.5 g with 37.2% purity).

The yield of 12-methytridecanal based on both steps (reduction and oxidation of 27.4 g<1 g/L fat extract with 30.4 GC-% 12-methyltric acid methyl ester and 17.8 g>1 g/L with 27.1 GC-% ester) was 34% based on the fractions 5 to 12 (4.1 g, purity 94.7%).

Based on the 95% purity of fractions 5, 7 and 9 to 12 (3.6 g), the yield after both steps was 30%.

The invention claimed is:

1. A method for producing branched aldehydes comprising:
   (a) providing a culture of one or more fungi of the genus *Conidiobolus*, wherein the one or more fungi is selected from the group consisting the species of *C. denaeosporus* and *C. heterosporus*, and producing biomass containing branched carboxylic acids in free form and/or bound form;
   (b) extracting the biomass from step (a) to produce a first intermediate containing free and/or bound carboxylic acids;
   (c) optionally chemically, enzymatically, or microbially hydrolyzing the bound carboxylic acids from the first intermediate;
   and
   (d) treating the first intermediate with a reducing agent of a chemical nature to convert the free and/or bound carboxylic acids into the corresponding alcohols and optionally separating one or more alcohols from interfering by-products and producing the chemically produced second intermediate containing these alcohols as a mixture or in enriched form;
   and
   (e) treating the chemically produced second intermediate with an oxidizing agent of a chemical nature to convert the free and/or bound alcohols into the corresponding aldehydes;
   or
   (f) treating the first intermediate with a reducing agent of a biological nature to convert the free and/or bound carboxylic acids into the corresponding aldehydes having the same number of carbon atoms compared to the free and/or bound carboxylic acids or into the corresponding aldehydes having a reduced number of carbon atoms by one compared to the free and/or bound carboxylic acids and producing the biologically produced second intermediate containing these aldehydes;
   and optionally
   (g) removing interfering by-components from the fractions obtainable after step(s) (d) and/or (e) and/or (f).

2. The method according to claim 1, wherein the branched aldehydes have 12 to 18 carbon atoms.

3. The method according to claim 1, wherein the branched aldehydes have a branched methyl group.

4. The method according to claim 1, wherein the aldehydes include 12-methyltridecanal, 12-methyltetradecanal, 14-methylpentadecanal, 16-methyloctadecanal, or mixtures thereof.

5. The method according to claim 1, wherein the first intermediate is subjected to hydrolysis before reduction.

6. The method according to claim 1, wherein, in step (d), the reduction is carried out with lithium alanate or sodium borohydride.

7. The method according to claim 1, wherein, in step (f), the reduction is carried out by a biological system.

8. The method according to claim 7, wherein the reduction is carried out with an aldehyde dehydrogenase.

9. The method according to claim 7, wherein the reduction is carried out with an α-dioxygenase.

10. The method according to claim 7, wherein the reduction is carried out with purified enzyme Nsp-CAR and/or MmFad9.

11. The method according to claim 7, wherein the reduction is carried out with a whole cell extract of cells expressing Nsp-CAR and/or MmFad9.

12. The method according to claim 7, wherein the reduction is carried out with viable cells capable of expressing the enzymes Nsp-CAR and/or MmFad9.

13. The method according to claim 1, wherein the reduction is carried out at a temperature in the range from 15 to 25° C.

14. The method according to claim 1, wherein, in step (e), 2,2,6,6-tetramethylpiperidinyloxyl (TEMPO) is used as the oxidizing agent.

15. The method according to claim 14, wherein the TEMPO is used together with an alkali bromide and an alkali hypochlorite.

16. The method according to claim 15, wherein the TEMPO, the alkali bromide, and the alkali hypochlorite are used in a molar ratio of about 1:(2 to 10):(10 to 40).

17. The method according to claim 1, wherein the oxidation is carried out at a temperature in the range from −5 to +10° C.

18. The method according to claim 1, wherein the reduction product, the oxidation product, or both are subjected to a distillation step.

* * * * *